(12) United States Patent
Perrier et al.

(10) Patent No.: US 11,754,544 B2
(45) Date of Patent: Sep. 12, 2023

(54) BULK MODULUS TESTING APPARATUS

(71) Applicant: Mueller International, Inc., Atlanta, GA (US)

(72) Inventors: Sebastien Perrier, Toronto (CA); Bruce Robertson, Toronto (CA); Valentin Mircea Burtea, Toronto (CA)

(73) Assignee: Mueller International, LLC, Atlanta, GA (US)

( * ) Notice: Subject to any disclaimer, the term of this patent is extended or adjusted under 35 U.S.C. 154(b) by 395 days.

(21) Appl. No.: 17/187,525

(22) Filed: Feb. 26, 2021

(65) Prior Publication Data
US 2022/0276213 A1 Sep. 1, 2022

(51) Int. Cl.
*G01N 33/18* (2006.01)
*G01N 29/036* (2006.01)

(52) U.S. Cl.
CPC .......... *G01N 33/18* (2013.01); *G01N 29/036* (2013.01); *G01N 2291/0228* (2013.01)

(58) Field of Classification Search
CPC ................. G01N 33/18; G01N 29/036; G01N 2291/0228; G01N 2291/022; G01N 2291/02827; G01N 29/045; G01N 29/14
See application file for complete search history.

(56) References Cited

U.S. PATENT DOCUMENTS

| | | | | | |
|---|---|---|---|---|---|
| 3,620,083 | A | * | 11/1971 | Dimeff et al. | ........ G01L 9/0072 73/702 |
| 4,055,764 | A | * | 10/1977 | Dimeff | .................. G01N 21/37 250/336.1 |
| 6,561,032 | B1 | | 5/2003 | Hunaidi | |
| 7,328,618 | B2 | | 2/2008 | Hunaidi et al. | |
| 7,475,596 | B2 | | 1/2009 | Hunaidi et al. | |
| 9,835,592 | B2 | | 12/2017 | Yusuf et al. | |
| 9,869,659 | B2 | * | 1/2018 | Buckland | ............. G01N 29/022 |
| 2019/0242851 | A1 | * | 8/2019 | Sinha | ................... G01N 29/024 |

* cited by examiner

*Primary Examiner* — Francis C Gray
(74) *Attorney, Agent, or Firm* — Taylor English Duma LLP

(57) ABSTRACT

Apparatuses, methods, and systems for accurate measurement of the bulk modulus of a fluid in a fluid distribution system. An apparatus comprises a pipe, a first endcap, and a second endcap defining a cylindrical cavity, a means for filling the cylindrical cavity with a fluid sample, and a vibrational sensor coupled to an end plate of the second endcap and communicatively connected to a water property measurement system. The vibrational sensor is operable to, subsequent to the filling of the cylindrical cavity with the fluid sample, send a signal representative of sensed vibrations in the end plate of the second endcap to the water property measurement system while an end plate of the first endcap is excited. The water property measurement system computes a frequency response function from the signal and determines a bulk modulus value for the fluid sample based on the frequency response function.

20 Claims, 5 Drawing Sheets

BULK MODULUS TESTING APPARATUS

BRIEF SUMMARY

The present disclosure relates to technologies for accurately measuring the bulk modulus of a fluid in a fluid distribution system. According to some embodiments, an apparatus comprises a pipe defining a cylindrical cavity, a first endcap enclosing the cylindrical cavity at a first end of the pipe, and a second endcap enclosing the cylindrical cavity at an opposite end of the pipe. The apparatus further comprises a means for filling the cylindrical cavity with a fluid sample and a vibrational sensor coupled to an end plate of the second endcap and communicatively connected to a water property measurement system. The vibrational sensor is operable to, subsequent to the filling of the cylindrical cavity with the fluid sample, send a signal representative of sensed vibrations in the end plate of the second endcap to the water property measurement system while an end plate of the first endcap is excited. The water property measurement system computes a frequency response function from this signal and determines a bulk modulus value for the fluid sample based on the frequency response function.

According to further embodiments, a method comprises filling a cylindrical cavity of a testing apparatus with a fluid sample taken from a pipe network, the testing apparatus comprising pipe, a first endcap, and a second endcap defining the cylindrical cavity. The fluid sample in the cylindrical cavity is excited while signal data from a vibrational sensor coupled to the second endcap is recorded, the signal data representative of sensed vibrations in an end plate of the second endcap. A frequency response function is computed from the recorded signal data and a bulk modulus of the fluid sample is determined based on the computed frequency response function.

According to further embodiments, a system for accurately measuring the bulk modulus of a fluid in a pipe network comprises a testing apparatus and a water property measurement system. The testing apparatus comprises a pipe, a first endcap, and a second endcap defining a cylindrical cavity; a means for filling the cylindrical cavity with a fluid sample; and a vibrational sensor coupled to an end plate of the second endcap. The water property measurement system comprises a processor, a sensor interface coupled to the processor and communicatively connected to the vibrational sensor, and a memory coupled to the processor. The memory contains processor-executable instructions that cause the processor to, subsequent to the filling of the cylindrical cavity with the fluid sample, receive a signal representative of sensed vibrations in the end plate of the second endcap of the testing apparatus while the fluid sample in the cylindrical cavity is excited, compute a frequency response function from the signal, and determine a bulk modulus value for the fluid sample based on the frequency response function.

These and other features and aspects of the various embodiments will become apparent upon reading the following Detailed Description and reviewing the accompanying drawings.

BRIEF DESCRIPTION OF THE DRAWINGS

In the following Detailed Description, references are made to the accompanying drawings that form a part hereof, and that show, by way of illustration, specific embodiments or examples. The drawings herein are not drawn to scale. Like numerals represent like elements throughout the several figures.

DETAILED DESCRIPTION

Figure 1:
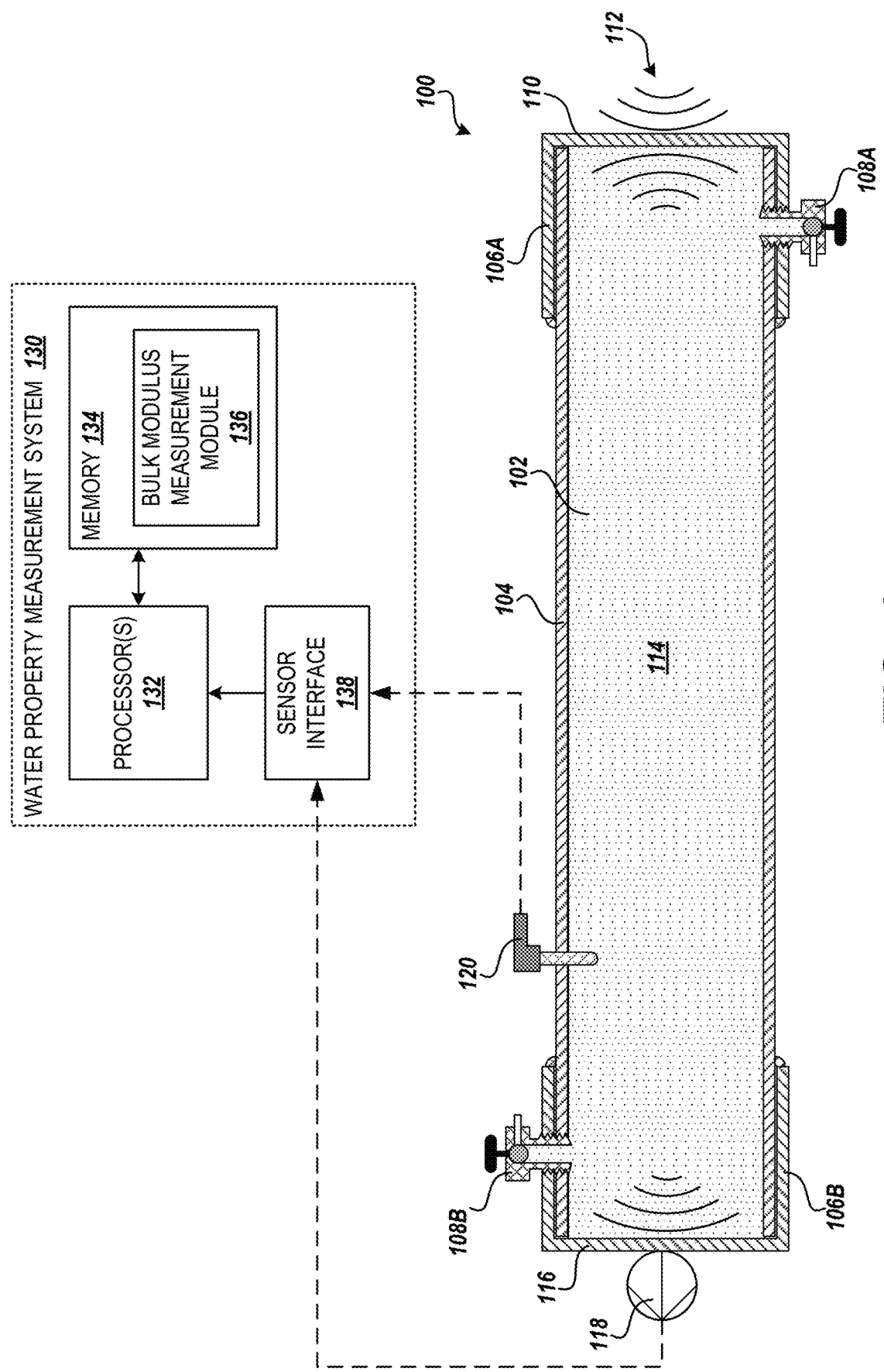
FIG. 1 comprises a cross-sectional view of an exemplary apparatus and a block diagram showing system components for accurate measurement of the bulk modulus of a fluid in a fluid distribution system, according to embodiments presented herein.

The following detailed description is directed to technologies for accurately measuring the bulk modulus of a fluid in a fluid distribution system. Utilizing the technologies described herein, personnel investigating the pipe network(s) of the fluid distribution system may improve predictions of the condition of pipes by obtaining accurate measurements of the bulk modulus of the fluid in the pipes being assessed. Water distribution mains may degrade in several ways. For example, metal pipe walls may corrode and become thinner and weaker (less stiff). Asbestos cement pipes lose calcium and the wall loses strength in time. The wall of pre-stressed concrete pipes gets weaker if the steel wires break. These degradations may cause hydraulic failure of the distribution system.

As described in, e.g., U.S. patent application Ser. No. 09/570,922, filed May 15, 2000, and issued as U.S. Pat. No. 6,561,032; U.S. patent application Ser. No. 11/156,573, filed Jun. 21, 2005, and issued as U.S. Pat. No. 7,328,618; and U.S. patent application Ser. No. 11/952,582, filed Dec. 7, 2007, and issued as U.S. Pat. No. 7,475,596, the disclosures of which are incorporated herein by this reference in their entireties, methods for assessing the condition of, e.g., predicting the stiffness and/or wall thickness of, pipes of a water or other fluid distribution system may rely on measuring the speed of sound in a given pipe segment. In one example, the speed of sound may be determined by placing two acoustic or vibration sensors on the pipe or a component of the water system bracketing the pipe segment under test, and then generating noise in the pipe segment. The noise propagates along the pipe segment reaching the first and second sensors at different times. The signals from the two sensors are recorded, and signal processing is applied to estimate a time delay between the noise reaching the two sensors. With the distance between the two sensors known and the estimated time delay, one can determine the propagation velocity of the noise down the pipe segment.

The condition of the pipe segment may then be determined by applying a mathematical model that relates the pipe condition to the propagation velocity. For example, a mathematical formula for the speed of sound in fluid filled pipes may be utilized, such as:

$$v = \frac{\sqrt{\frac{K}{\rho}}}{\sqrt{1 + \frac{DK}{tE}}}$$

where D is the diameter of the pipe, t is the wall thickness, E is the elastic modulus of the pipe material, v is the measured speed of sound, ρ is the density of the fluid within, and K is the bulk modulus of elasticity of the fluid.

The accuracy of the condition assessment of the pipe segment therefore relies on knowing precise values for the specific parameters, including the bulk modulus K of the fluid in the pipe. The bulk modulus of a liquid is a measure of how resistant to compression the substance is and can vary based on an amount of air content of the fluid, mineral content of the fluid, the temperature of the fluid, and the like. Because of these variations, accurate determination of pipe condition requires knowing the precise bulk modulus of the fluid in the pipes under test at the time of testing. One method of measuring the bulk modulus of the fluid in the pipes involves measuring the speed of sound in a segment of pipe of known specifications and known condition, e.g., new. The bulk modulus may then be determined from the speed using the same mathematical model described above. However, this calibration approach has certain limitations as there are sites for which it may be difficult to find a suitable pipe of known condition.

According to embodiments described herein, the accuracy of condition assessment of pipes in a fluid distribution system may be improved by utilizing an apparatus to perform accurate measurements of the bulk modulus of the fluid in the pipes at the time of testing. The apparatus presented herein measures the bulk modulus of a fluid directly using the principle of acoustic resonance. The apparatus can be used in the field to measure the bulk modulus of the fluid, such as water in a water distribution network, by taking water samples from the specific pipe network under test. By utilizing a vessel of precise and known dimensions, the bulk modulus of the water can be accurately determined by computing a frequency response function of the vessel when filled with the sampled water, as the resonant frequencies of the water in the vessel will vary with its bulk modulus. By identifying one or more resonant frequencies of the fluid (water), also referred to herein as "acoustic modes," from the frequency response function, the bulk modulus of the water sample can be determined.

FIG. 1 shows a cross-section of an exemplary bulk modulus test apparatus 100, according to some embodiments. In some embodiments, the bulk modulus test apparatus 100 may include a cylindrical cavity 102 defined by a pipe 104 of known material and dimensions. According to embodiments, the dimensions of the pipe 104 are chosen to optimize the frequency response and maximize the dynamic response of acoustic resonance of fluid in the cylindrical cavity in the desired frequency ranges. For example, as will be described below, for a bulk modulus test apparatus 100 optimized to measure bulk modulus values K ranging from 1.7 GPa to 2.2 GPa with acoustic mode frequencies in the ranges of 850-866 Hz and 1324-1399 Hz, the standing wave formula F=v/2L may result in an optimized length for the pipe 104 of about 21" (~0.54 m). Similarly, the diameter of the inner diameter of the pipe 104 may be optimized to boost the dynamic response (i.e., amplitude) of the resonance in these frequency ranges, resulting in a pipe of 4" (101.6 mm) inner diameter.

The length and diameter of the pipe 104 and other dimensions selected for the bulk modulus test apparatus 100 also ensure the frequency range for the acoustic mode(s) of interest are well separated from the vibration modes of the structure of the apparatus, determined from finite element modeling and/or testing of the apparatus. For example, a bulk modulus test apparatus 100 as shown with the dimensions provided may have multiple vibration modes of 1119 Hz, 1458 Hz, 1606 Hz, etc., which are distinct from the acoustic modes in the ranges of 850-866 Hz and 1324-1399 Hz for water in the cylindrical cavity 102, as will be described in more detail below.

Because the bulk modulus test apparatus 100 is a pressure vessel, the materials, wall thickness, and other parameters of the structure must also take into account the pressure(s) of the fluid in the cylindrical cavity 102 required for operation. According to some embodiments, the pipe 104 may comprise extruded 6061-T6 aluminum tubing of specific length and ¼" (~6.4 mm) wall thickness. The cylindrical cavity 102 may be enclosed by two endcaps 106A and 106B of same or similar materials and dimensions at either end of the pipe 104. For example, the endcaps 106A, 106B may comprise of 5" (127 mm) outer diameter 6061-T6 cylindrical aluminum bar milled to fit over the end of the pipe 104. The endcaps 106A, 106B may be welded or otherwise bonded to the outer wall of the pipe 104 to create a watertight cylindrical cavity 102.

It will be appreciated that the materials and dimensions described here are for illustrative purposes only, and any number of materials and dimensions will be apparent to one skilled in the art that would be suitable for the purpose described herein, as long as the parameters of the materials (e.g., elastic modulus E) and the dimensions (e.g., cavity diameter and length, wall thickness t) can be precisely determined. It is intended that all such materials and dimensions be included in the scope of this disclosure.

According to further embodiments, the bulk modulus test apparatus 100 also includes one or more valves, such as valves 108A and 108B, that allow the cylindrical cavity 102 to be filled with the water samples taken at the pipes under test. For example, one valve 108B could be used to fill the cylindrical cavity 102 with the sampled water 114 while another valve 108A could be used to evacuate the air from the cavity as it is filled. It will be appreciated that excess air bubbles in the cylindrical cavity 102 may affect bulk modulus testing of the sampled water 114 in the bulk modulus test apparatus 100.

Figure 2:
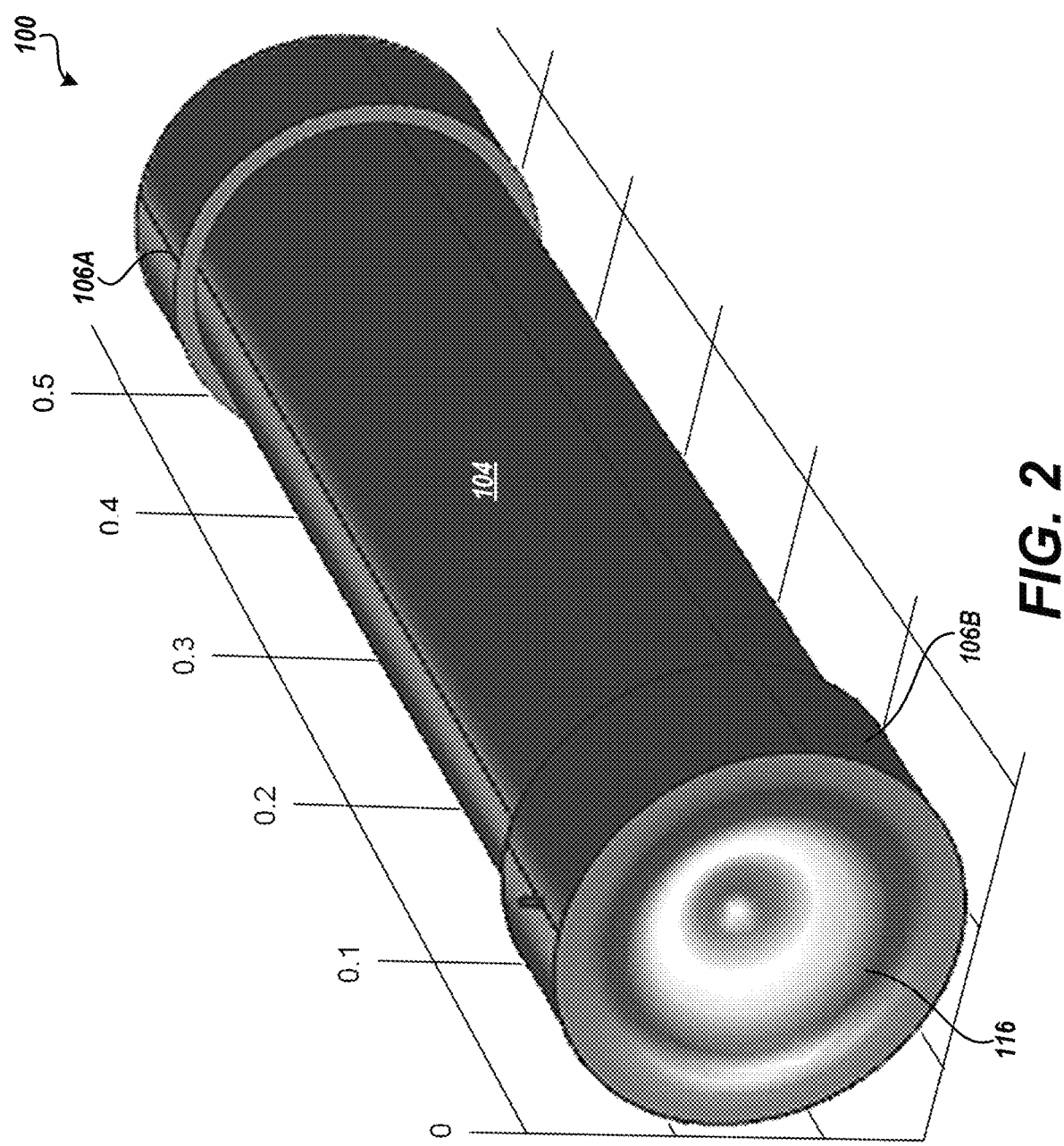
FIG. 2 is a perspective view showing further details of the apparatus for accurate measurement of the bulk modulus of a fluid in a fluid distribution system, according to embodiments presented herein.

According to embodiments, once the cylindrical cavity 102 is filled with water sample 114 from the pipes under test and any excess air is purged, the end plate 110 of one endcap 106A is excited, as shown at 112, to produce acoustic resonance in the fluid (water) inside of the cavity. For example, the end plate of 110 of the endcap 106A may be excited by tapping with a hammer or other impact device on the outside surface of the end plate. In another example, the end plate 110 of the endcap 106A may be excited through a range of frequencies by a mechanical actuator, such as a speaker or piezoelectric transducer. The acoustic resonance of the fluid in turn causes the end plate 116 of the opposite end cap 106B to deform (vibrate) axially. A perspective view of the bulk modulus test apparatus 100 is shown in FIG. 2 showing the axial vibration of the end plate 116 of the opposite end cap 106B from the excitation at the end of the pipe 104.

Returning to FIG. 1, a vibrational sensor 118 is coupled to the endcap 106B to sense the vibrations in the end plate 116. In some embodiments, the vibrational sensor 118 may comprise an accelerometer installed on the outside surface of the end plate 116 substantially along a center axis of the cylindrical cavity 102 in order to receive maximum deflection from vibrations creating the highest resolution signal data from the acoustic resonance. In further embodiments, the vibrational sensor 118 may comprise a piezoelectric transducer, accelerometer, optical displacement sensor, acoustic pressure sensor (microphone), eddy current or capacitive displacement sensor, or any combination of these and other sensors known in the art for measuring vibrations from the outside surface of the end plate 116.

A signal representing the sensed vibrations from the vibrational sensor 118 is sent to a water property measurement system 130. The water property measurement system 130 may then process and analyze the signal to compute a frequency response function corresponding to the excitation (s) of the water sample 114 in the cylindrical cavity 102. As described herein, different values of the bulk modulus K of the sampled water will make the fluid-filled cylindrical cavity 102 and end plate 116 resonate at different frequencies. By computing a frequency response function from the vibrations of the end plate 116, one or more acoustic modes may be identified, and a precise value of the bulk modulus of the water sample 114 taken from the pipes under test may be determined.

In some embodiments, the water property measurement system 130 may comprise a mobile computing device, such as a laptop or tablet, deployed in the field in proximity to be used at the source of the sampled water. Alternatively or additionally, the water property measurement system 130 may comprise laptop or desktop computers; tablets, smartphones or mobile devices; server computers hosting application services, web services, database services, file storage services, and the like; and virtualized, cloud-based computing resources, such as processing resources, storage resources, and the like, that receive the signal data from the vibrational sensor 118 through one or more intermediate communication links or networks.

According to embodiments, the water property measurement system 130 includes one or more processor(s) 132. The processor(s) 132 may comprise microprocessors, microcontrollers, FPGAs, cloud-based processing resources, or other processing resources capable executing instructions and routines stored in a connected memory 134. The memory 134 may comprise a variety non-transitory computer-readable storage media for storing processor-executable instructions, data structures and other information within the water property measurement system 130, including volatile and non-volatile, removable and non-removable storage media implemented in any method or technology, such as RAM; ROM; FLASH memory, solid-state disk ("SSD") drives, or other solid-state memory technology; compact disc ROM ("CD-ROM"), digital versatile disk ("DVD"), or other optical storage; magnetic hard disk drives ("HDD"), hybrid solid-state and magnetic disk ("SSHD") drives, magnetic tape, magnetic cassette, or other magnetic storage devices; and the like.

In some embodiments, the memory 134 may include a bulk modulus measurement module 136 for performing the analysis of the signal data from the vibrational sensor 118 to determine the frequency response function and the corresponding bulk modulus of the water sample 114 in the cylindrical cavity 102, as described herein. The bulk modulus measurement module 136 may include one or more software programs, components, and/or modules executing on the processor(s) of the water property measurement system 130. The bulk modulus measurement module 136 may further include hardware components specifically designed to perform one or more steps of the routines described herein. According to further embodiments, the memory 134 may store processor-executable instructions that, when executed by the processor(s) 132, perform some or all of the steps of the routine 500 described herein for accurately measuring the bulk modulus of a fluid in a fluid distribution system, as described in regard to FIG. 5.

The water property measurement system 130 may be in direct communication with the vibrational sensor 118 over a wired connection, or may be indirectly connected to the sensors and impulse generator through one or more intermediate communication links and/or computing devices. For example, a laptop may be connected to the vibrational sensors 118 via one or more radio-frequency ("RF") links to receive the signal from the sensor in real-time. In other embodiments, the signal from the vibrational sensor 118 may be received by an individual computing device (referred to as a "node"), recorded, and then sent to a central analysis computer for processing and analysis.

According to some embodiments, the processor(s) 132 are operatively connected to the vibrational sensor 118 through a sensor interface 138. The sensor interface 138 allows the processor(s) 132 to receive the signal from the vibrational sensor 118 representative of the sensed vibrations in the end plate 116 of the endcap 106B. For example, the sensor interface 138 may utilize one or more analog-to-digital converters ("ADCs") to convert an analog voltage output of the vibrational sensor 118 to a digital value that is sampled by the processor(s) 132 at a specific sampling rate sufficient to represent the frequency response function in the resulting signal data. According to some embodiments, a sampling rate of around 10 kHz may be utilized to capture data from which the frequency response function can be calculated. For example, sampling rates of 8192 Hz or 11025 Hz may be utilized to match the sampling rates of pipe condition assessment testing apparatuses where the determined bulk modulus value K will be utilized. In further embodiments, an audio processing circuit or "sound card" of the laptop computer may be utilized to provide the sampling functionality.

The water property measurement system 130 utilizes the signal data to determine a frequency response function for the end plate of the endcap 106B in response to the excitations at 112. According to embodiments, computing the frequency response function includes performing a Fourier transform on the signal data to convert it from a time domain to a frequency domain. In further embodiments, filters may be applied to filter out vibrational modes of the apparatus. From the frequency response function, a resonant frequency of the one or more acoustic modes may be identified, and the bulk modulus value K of the water sample 114 may be determined from the frequency of the acoustic mode(s).

Figure 3:
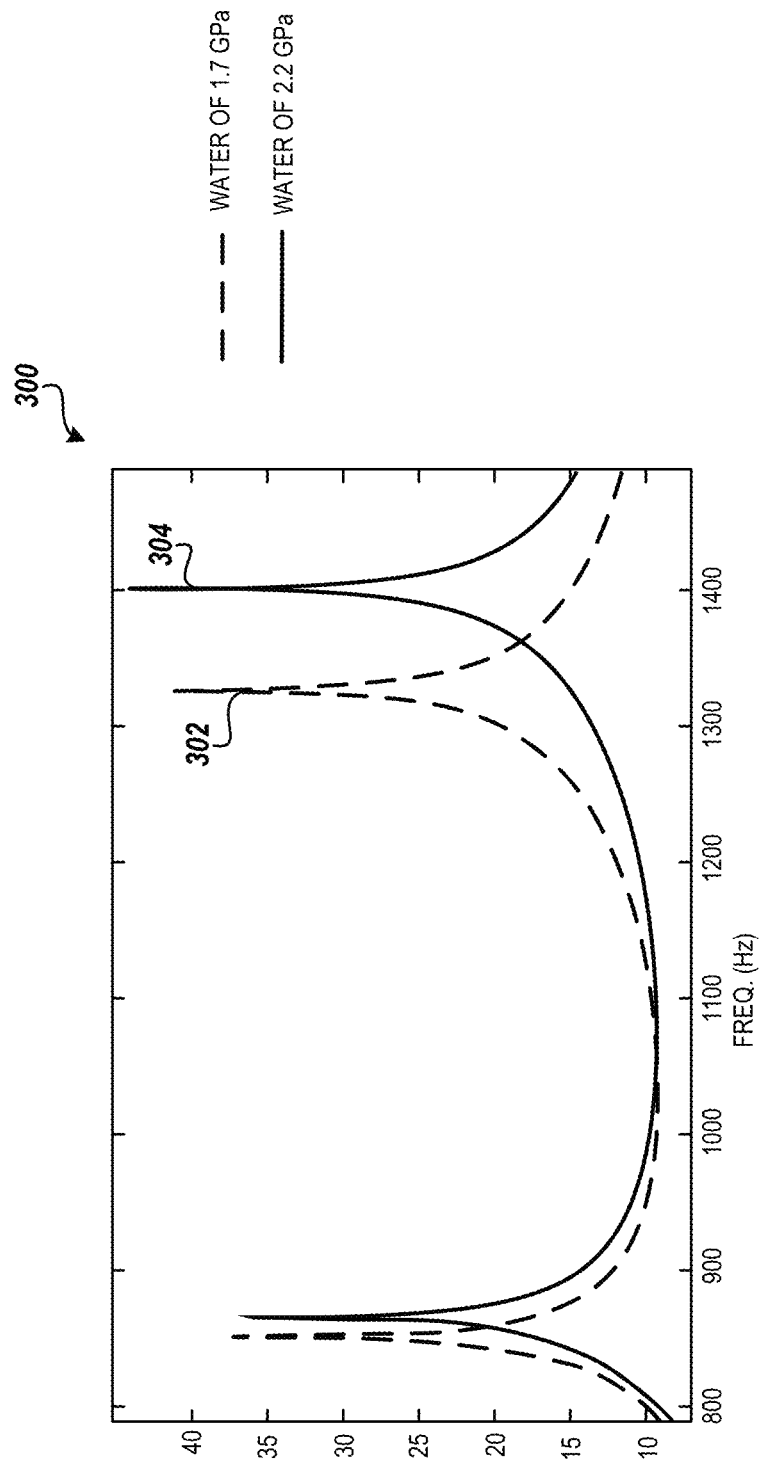
FIG. 3 is a graph showing two frequency response functions for the apparatus filled with fluids having two different bulk modulus values, according to embodiments presented herein.

FIG. 3 shows a graph 300 of exemplary frequency response functions 302 and 304 by frequency computed from signal data from the bulk modulus test apparatus 100 for water samples 114 with two distinct bulk modulus values. The first frequency response function 302 results from excitation of the bulk modulus test apparatus 100 filled with water 114 with a bulk modulus value K of 1.7 GPa and comprises two principal acoustic resonances at 850 Hz and 1324 Hz. The second frequency response function 304 results from excitation of the apparatus filled with water 114 with a bulk modulus value K of 2.2 GPa and comprises acoustic resonances at 866 Hz and 1399 Hz. As may been seen in the graph 300, the second acoustic resonance(s), or "second acoustic mode," at 1324 Hz and 1399 Hz of the respective frequency response functions 302 and 304 provide better resolution for determining variation in resonant frequency for water samples 114 with different bulk modulus values K than the first acoustic resonance(s), or "first acoustic mode," at 850 Hz and 866 Hz, and therefore the second acoustic mode may be utilized to determine the bulk modulus value K for the sample contained inside the cylindrical cavity 102, according to some embodiments.

For example, the water property measurement system 130 may include a table mapping certain acoustic mode frequencies to specific bulk modulus values K. The table may be generated by a finite element model of the bulk modulus test apparatus 100 with a specific set of dimensions and verified and/or adjusted by one or more calibration tests. The table may be stored in the memory 134 of the water property measurement system 130 and comprise a discrete set of acoustic mode frequency and bulk modulus value pairs within the range of testing of the apparatus, e.g., 1.7 GPa to 2.2 GPa, such as those shown in Table 1 below. The table may be accessed by the bulk modulus measurement module 136 to retrieve the bulk modulus value K for the water sample 114 being tested based on the frequency of the selected acoustic mode (e.g., the second acoustic mode) identified in the frequency response function computed from signal data from the bulk modulus test apparatus 100. In further embodiments, if the identified acoustic mode frequency value is not in the table, the bulk modulus measurement module 136 may utilize linear interpolation from two adjacent table entries to compute the bulk modulus value K for the water sample 114.

TABLE 1

| Acoustic Mode Freq. (Hz) | Bulk Modulus Value K (GPa) |
|---|---|
| 1324 | 1.70 |
| 1331.5 | 1.75 |
| 1339 | 1.80 |
| 1346.5 | 1.85 |
| 1354 | 1.90 |
| . . . | . . . |
| 1399 | 2.20 |

It will be appreciated that other methods of mapping the frequency of an acoustic mode to a bulk modulus value will be apparent to one skilled in the art upon reading this disclosure, including using a mathematical model or relationship determined by finite element modeling and/or testing of the apparatus. In further embodiments, the bulk modulus value K for the water sample 114 may be determined from the frequency response function computed from the signal data from the bulk modulus test apparatus 100 utilizing some other method beyond mapping a frequency of a selected acoustic mode to a bulk modulus value. For example, the frequencies of two or more acoustic modes in the frequency response function may be identified and utilized to calculate the bulk modulus value K for the water sample 114, or the frequency response function may be compared to frequency response functions stored for various bulk modulus values through correlation in order to determine the closest match, providing for influence of an arbitrary number of acoustic modes to be reflected. It is intended that all such methods of determining the bulk modulus value from the frequency response function be included in the scope of this disclosure.

Figure 4:
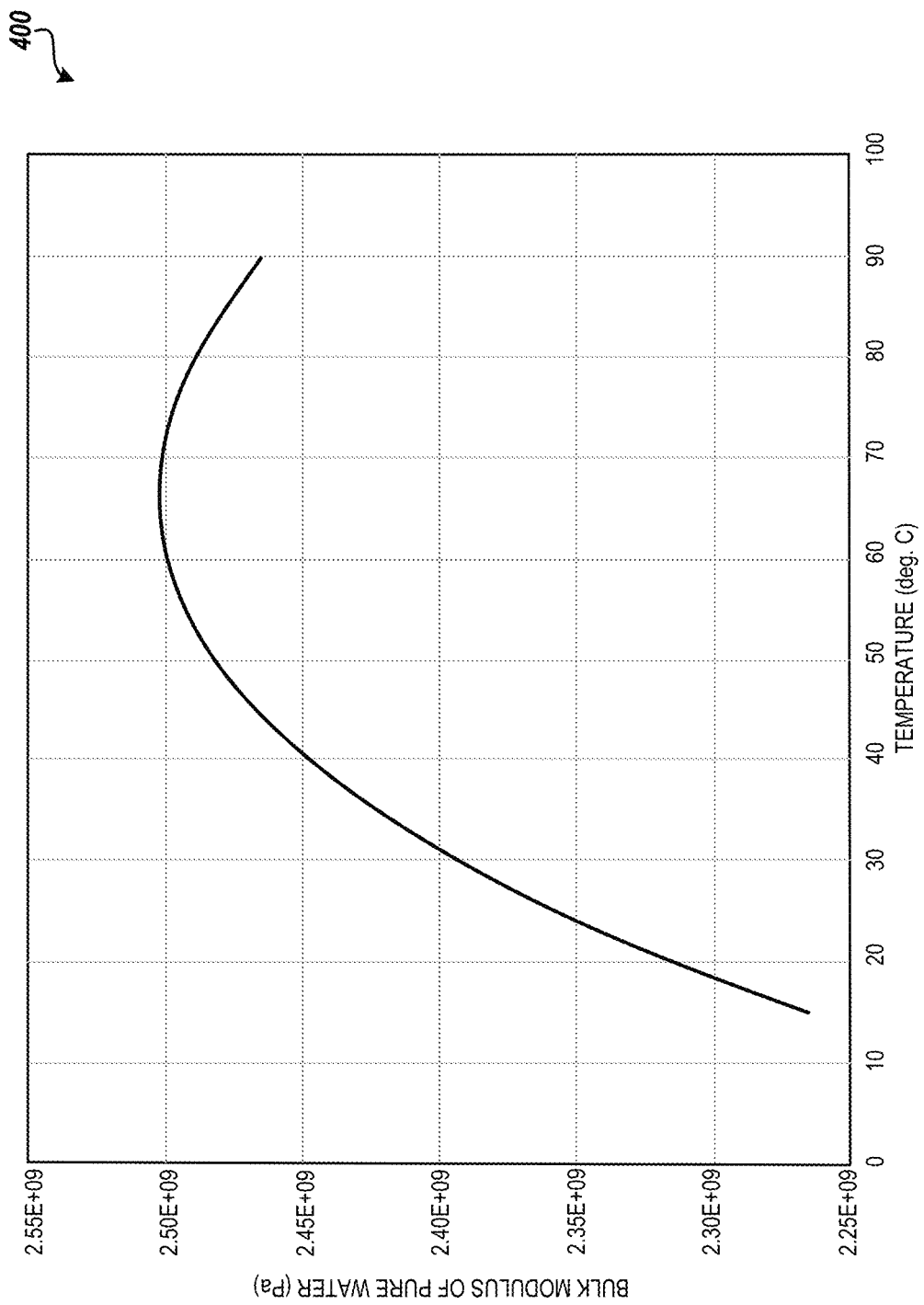
FIG. 4 is a graph showing a variation of the bulk modulus of pure water based on temperature, according to embodiments presented herein.

According to further embodiments, the temperature of the water sample 114 inside the cylindrical cavity 102 is also measured as the bulk modulus K of water varies with temperature. For example, the graph 400 of FIG. 4 shows the variation of the bulk modulus with temperature of pure water containing no air. According to some embodiments, the temperature of the water 114 filling the cylindrical cavity 102 of the bulk modulus test apparatus 100 may be read concurrently with the bulk modulus measurement process from a temperature sensor 120 in direct contact with the water or in thermal contact with the water through the wall of the pipe 104. The temperature reading may be read from the temperature sensor 120 by the water property measurement system 130 through the same or similar sensor interface 138 as the vibrational sensor 118. In other embodiments, the temperature value for the water sample 114 may be obtained from some other source and entered manually into the water property measurement system 130 for determination of the bulk modulus value of the water under test. Utilizing the measured temperature value for the water sample 114 and the bulk modulus variation by temperature data of pure water from the graph 400 of FIG. 4 allows the computed bulk modulus value K of the sample to be adjusted as required for condition assessment based on differing temperature of the water in the pipes of the pipe network under test.

It will be appreciated that the structure and/or functionality of the water property measurement system 130 may be different than that illustrated in FIG. 1 and described herein. For example, one or more of the processor(s) 132, memory 134, sensor interfaces 138, and/or other components and circuitry described may be integrated within a common integrated circuit package or distributed among multiple integrated circuit packages in one or more computing devices. In some embodiments, some or all of the processing and analysis described herein may be implemented as software applications on mobile computing platforms, such as a smartphone or laptop with cellular networking capability. Similarly, the illustrated connection pathways are provided for purposes of illustration and not of limitation, and some components and/or interconnections may be omitted for purposes of clarity. It will be further appreciated that water property measurement system 130 may not include all of the components shown in FIG. 1 may include other components that are not explicitly shown in FIG. 1 or may utilize architectures completely different than those shown in FIG. 1.

Figure 5:
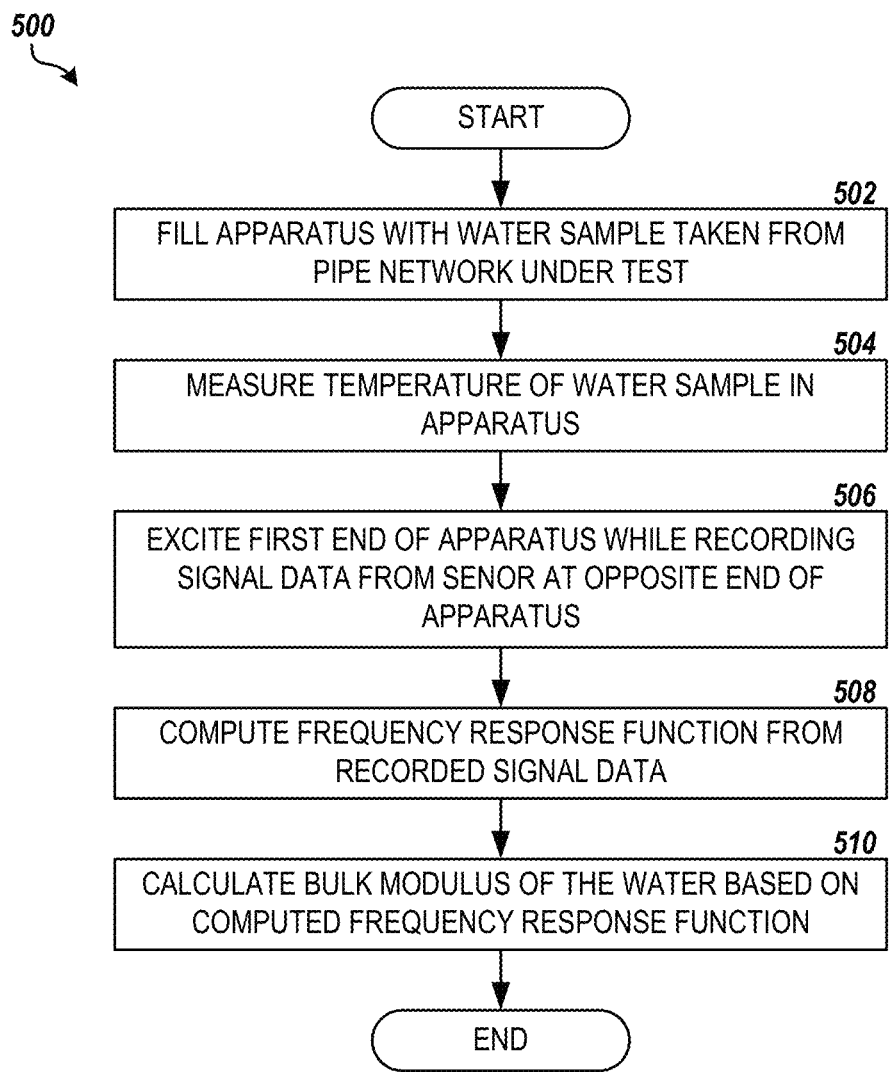
FIG. 5 is a flow diagram showing one routine for accurately measuring the bulk modulus of a fluid in a fluid distribution system, according to embodiments presented herein.

FIG. 5 illustrates one routine 500 for accurately measuring the bulk modulus of a fluid sample taken from a pipe network in the bulk modulus test apparatus 100, according to some embodiments. In some embodiments, parts of the routine 500 may be performed by the bulk modulus measurement module 136 executing on a laptop computer in the field directly connected to the bulk modulus test apparatus 100, more specifically to the vibrational sensor 118 and, potentially, the temperature sensor 120 of the apparatus. In other embodiments, the routine 500 may be performed by some combination of the processor(s) 132, computing devices, components, and modules of the water property measurement system 130 in conjunction with procedures, parameters, data, and/or instructions provided by maintenance personnel utilizing the bulk modulus test apparatus 100 in conjunction with the condition assessment of pipes of a fluid distribution system.

The routine 500 begins at step 502, where the cylindrical cavity 102 of the bulk modulus test apparatus 100 is filled with a fluid sample taken from the fluid distribution system. For example, a water sample 114 may be obtained from a pipe network of a water distribution system in proximity to pipes being targeted for condition assessment. The water sample may be obtained from a hydrant connected to the pipe network and fed into the cylindrical cavity 102 through one valve 108A of the bulk modulus test apparatus 100 while a second valve 108B of the apparatus is controlled to allow displaced air to escape. Feeding the water directly from the pipe network may provide for the water sample 114 in the cylindrical cavity 102 to closely duplicate the temperature, pressure, air content, mineral content, and other qualities of the water in the pipes.

Once the cylindrical cavity 102 of the bulk modulus test apparatus 100 is filled with the sampled water, the routine 500 proceeds from step 502 to step 504, where a temperature of the water sample 114 is determined. According to some embodiments, the temperature may be read by the bulk modulus measurement module 136 directly from a temperature sensor 120 of the bulk modulus test apparatus 100 in contact with the water sample 114. In other embodiments, the temperature value may be determined by other means and provided to the bulk modulus measurement module 136.

From step 504, the routine 500 proceeds to step 506, where the end plate 110 of the endcap 106A at a first end of the apparatus is excited while signal data is recorded from the vibrational sensor 118 coupled to the endcap 106B at the opposite end of the apparatus. According to some embodiments, the end plate of 110 the endcap 106A may be excited by tapping with a small hammer or rigid object on the outside surface of the end plate. In other embodiments, the end plate 110 may be excited through a range of frequencies by a mechanical actuator, such as a speaker or piezoelectric transducer. Signal data is obtained from the vibrational sensor 118 coupled to the endcap 106B during the excitation of the end plate 110 and temporarily stored in the water property measurement system 130. For example, the vibrational sensor 118 may be connected to a microphone input of an audio processing circuit of the laptop and the signal digitally sampled by an ADC of the audio processing circuit for the period of excitation, with the samples stored in the memory 134 of the laptop.

The routine 500 proceeds from step 506 to step 508, where the bulk modulus measurement module 136 computes a frequency response function associated with the bulk modulus test apparatus 100 filled with the sampled water from the signal data. According to some embodiments, this includes performing a Fast Fourier Transform (FFT) of the signal data to convert the data from the time domain to the frequency domain. The routine 500 then proceeds to step 510, where the bulk modulus measurement module 136 determines a bulk modulus value K for the water in the bulk modulus test apparatus 100 based on the computed frequency response function. For example, as described above in regard to FIG. 1, the resonant frequency(s) of one or more acoustic modes may be identified from the frequency response function, and the bulk modulus value K of the water sample 114 may be determined from the acoustic mode frequency(s) by the bulk modulus measurement module 136 based on a table mapping acoustic mode frequencies to specific bulk modulus values K stored in the memory 134 of the water property measurement system 130. From step 510, the routine 500 ends.

Based on the foregoing, it will be appreciated that technologies for accurately measuring the bulk modulus of a fluid in a fluid distribution system are presented herein. While the methods, apparatuses, and systems described herein refer to the measurement of the bulk modulus of a water sample 114 taken from a water distribution system, the technologies described herein may be utilized with any fluid where accurate measurement of the bulk modulus in the field is needed, such as oil, gasoline, kerosene, seawater, and the like, with the dimensions, materials, and structure of the bulk modulus test apparatus 100 adjusted accordingly based on the range of bulk modulus values to be tested. The above-described embodiments are merely possible examples of implementations set forth for a clear understanding of the principles of the present disclosure. Many variations and modifications may be made to the above-described embodiments without departing substantially from the spirit and principles of the present disclosure. All such modifications and variations are intended to be included within the scope of the present disclosure, and all possible claims to individual aspects or combinations and sub-combinations of elements or steps are intended to be supported by the present disclosure.

The logical steps, functions or operations described herein as part of a routine, method or process may be implemented (1) as a sequence of processor-implemented acts, software modules or portions of code running on a controller or computing system and/or (2) as interconnected machine logic circuits or circuit modules within the controller or other computing system. The implementation is a matter of choice dependent on the performance and other requirements of the system. Alternate implementations are included in which steps, operations or functions may not be included or executed at all, may be executed out of order from that shown or discussed, including substantially concurrently or in reverse order, depending on the functionality involved, as would be understood by those reasonably skilled in the art of the present disclosure.

It will be further appreciated that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

What is claimed is:

1. An apparatus comprising:
   a pipe defining a cylindrical cavity;
   a first endcap enclosing the cylindrical cavity at a first end of the pipe, the first endcap comprising an end plate;
   a second endcap enclosing the cylindrical cavity at an opposite end of the pipe from the first end, the second endcap comprising an end plate;
   a means for filling the cylindrical cavity with a fluid sample; and
   a vibrational sensor coupled to the end plate of the second endcap and communicatively connected to a water property measurement system, the vibrational sensor operable to, subsequent to the filling of the cylindrical cavity with the fluid sample, send a signal representative of sensed vibrations in the end plate of the second endcap to the water property measurement system while the end plate of the first endcap is excited, the water property measurement system configured to compute a frequency response function from the signal and determine a bulk modulus of the fluid sample based on the frequency response function.

2. The apparatus of claim 1, further comprising:
a temperature sensor in thermal contact with the fluid sample and communicatively connected to the water property measurement system, the temperature sensor operable to provide a reading of the temperature of the fluid sample to the water property measurement system in conjunction with the determination of the bulk modulus of the fluid sample.

3. The apparatus of claim 1, wherein the vibrational sensor comprises an accelerometer located on an outer surface of the end plate of the second endcap substantially along a center axis of the cylindrical cavity.

4. The apparatus of claim 1, wherein a length and diameter of the pipe defining the cylindrical cavity is selected to optimize frequency and dynamic response of one or more acoustic modes of the fluid sample in the cylindrical cavity corresponding to a range of bulk modulus values of the fluid to be tested.

5. The apparatus of claim 4, wherein determining the bulk modulus of the fluid sample based on the frequency response function comprises identifying a frequency of at least one acoustic mode of the fluid sample in the cylindrical cavity from the frequency response function and mapping the frequency of the at least one acoustic mode to a bulk modulus value.

6. The apparatus of claim 1, wherein the end plate of the first endcap is excited by tapping an outer surface of the end plate of the first endcap with a hammer or other rigid instrument.

7. The apparatus of claim 1, wherein the pipe, the first endcap, and the second endcap comprise aluminum.

8. The apparatus of claim 1, wherein the water property measurement system comprises a portable computing device running a bulk modulus measurement module.

9. A method comprising steps of:
filling a cylindrical cavity of a testing apparatus with a fluid sample taken from a pipe network, the testing apparatus comprising pipe, a first endcap, and a second endcap defining the cylindrical cavity;
exciting the fluid sample in the cylindrical cavity while recording signal data from a vibrational sensor coupled to the second endcap, the signal data representative of sensed vibrations in an end plate of the second endcap;
computing a frequency response function from the recorded signal data; and
determining a bulk modulus of the fluid sample based on the computed frequency response function.

10. The method of claim 9, wherein determining the bulk modulus of the fluid sample based on the frequency response function comprises identifying a frequency of an acoustic mode of the fluid sample in the cylindrical cavity from the frequency response function and mapping the frequency of the acoustic mode to a bulk modulus value.

11. The method of claim 10, wherein mapping the frequency of the acoustic mode to the bulk modulus value comprises looking up the frequency in a table of acoustic mode frequency and bulk modulus value pairs.

12. The method of claim 10, wherein dimensions of the pipe defining the cylindrical cavity is selected to optimize frequency and dynamic response of the acoustic mode of the fluid sample in the cylindrical cavity corresponding to a range of bulk modulus values of the fluid to be tested.

13. The method claim 9, further comprising steps of:
measuring a temperature of the fluid sample in the cylindrical cavity; and
utilizing the temperature of the fluid sample to adjust the determined bulk modulus of the fluid sample for pipe condition assessment.

14. The method of claim 9, wherein the vibrational sensor comprises an accelerometer located on an outer surface of an end plate of the second endcap substantially along a center axis of the cylindrical cavity.

15. The method of claim 9, wherein exciting the fluid sample in the cylindrical cavity comprises tapping an outer surface of an end plate of the first endcap with a hammer or other rigid instrument.

16. A system comprising:
a testing apparatus comprising
a pipe, a first endcap, and a second endcap defining a cylindrical cavity,
a means for filling the cylindrical cavity with a fluid sample, and
a vibrational sensor coupled to an end plate of the second endcap; and
a water property measurement system comprising
a processor,
a sensor interface coupled to the processor and communicatively connected to the vibrational sensor, and
a memory coupled to the processor, the memory containing processor-executable instructions that cause the processor to, subsequent to the filling of the cylindrical cavity with the fluid sample, receive a signal representative of sensed vibrations in the end plate of the second endcap of the testing apparatus while the fluid sample in the cylindrical cavity is excited, compute a frequency response function from the signal, and determine a bulk modulus value for the fluid sample based on the frequency response function.

17. The system of claim 16, further comprising:
a temperature sensor in thermal contact with the fluid sample and communicatively connected to the sensor interface, the temperature sensor operable to provide a reading of the temperature of the fluid sample to the processor in conjunction with the determination of the bulk modulus value for the fluid sample.

18. The system of claim 16, wherein the vibrational sensor comprises an accelerometer located on an outer surface of the end plate of the second endcap substantially along a center axis of the cylindrical cavity.

19. The system of claim 16, wherein determining the bulk modulus value for the fluid sample based on the frequency response function comprises identifying a frequency of at least one acoustic mode of the fluid sample in the cylindrical cavity from the frequency response function and mapping the frequency of the at least one acoustic mode to a bulk modulus value.

20. The system of claim 16, wherein exciting the fluid sample in the cylindrical cavity comprises tapping an outer surface of an end plate of the first endcap with a hammer or other rigid instrument.

* * * * *